(12) United States Patent
Hager et al.

(10) Patent No.: US 6,172,203 B1
(45) Date of Patent: Jan. 9, 2001

(54) METHOD FOR EXTRACTING AND PURIFYING PULMONARY SURFACTANT

(76) Inventors: Alfredo Adolfo Hager; Tomas DePaoli, both of Cabrera 2365-San Justo, Buenos Aires, CP (1754) (AR)

(*) Notice: Under 35 U.S.C. 154(b), the term of this patent shall be extended for 0 days.

(21) Appl. No.: 08/742,977

(22) Filed: Nov. 1, 1996

(30) Foreign Application Priority Data

Feb. 7, 1996 (AR) .................................... 335.327

(51) Int. Cl.[7] .................................................. C07K 1/14
(52) U.S. Cl. ............................................. 530/412; 514/21
(58) Field of Search ............................. 424/557; 514/21; 530/412

(56) References Cited

U.S. PATENT DOCUMENTS

| | | | |
|---|---|---|---|
| 4,338,301 | * | 7/1982 | Tetsuro et al. ...................... 424/557 |
| 4,397,839 | * | 8/1983 | Tanaka ................................. 424/557 |
| 4,603,124 | * | 7/1986 | Takei et al. .............................. 514/78 |
| 5,024,995 | * | 6/1991 | Robertson et al. ..................... 514/21 |
| 5,552,161 | * | 9/1996 | Disse et al. ........................... 424/557 |

* cited by examiner

*Primary Examiner*—Michael Borin
(74) *Attorney, Agent, or Firm*—Fulbright & Jaworski L.L.P.

(57) ABSTRACT

It is obtained a chloroform solution that contains liposubles lipids and proteins extracted by means of a bronchio-alveolar washing of pigs, cows or sheep with slightly hypertonic solution. From the lyophilization of such chloroform solution it is obtained a product resuspensible in physiological solution that constitutes the exogenous pulmonary surfactant utilized in pulmonary therapeutics and also for the clinic research of the pulmonary function when it is associated with radionucleus, in particular with 99 mTc for pulmonary centellography.

9 Claims, No Drawings

METHOD FOR EXTRACTING AND PURIFYING PULMONARY SURFACTANT

BACKGROUND OF THE INVENTION

The exchange of oxygen and carbon dioxide between the inspired air and the blood to be oxygenated is done through the pulmonary alveoli which are grouped in racemes surrounded by a network of capillaries where the blood to be ventilated is circulating.

The exterior faces of such walls are covered with a very thin film, monomolecular, of a viscous tensioactive substance which is synthesized by the type II alveoli, which controls the alveoli expansion, reducing the tendency to collapse (that is to say, the occlusion) of the alveoli during the expiration phase.

On the other hand such a film, due to is tensioactive properties, facilitates the displacement of macrophages (alveolaris) that capture foreign elements trapped in this film (inspired particles, bacteria, viruses), that travel along the alveoli surface and move to the bronchial mucociliary zone.

This substance having tensioactives properties that covers the alveoli surface, named pulmonary surfactant (PS) is of complex composition, not completely elucidated; in addition it varies with age, health and also with the extraction method. In general, the PS extract from healthy persons and other mammals contains 90% lipids, 80% of which are phospholipids and the remainder neutral lipids, mainly cholesterol. Phospholypic fraction in mammals in general.

In addition to the lipid fraction mentioned, the PS have a protein fraction from which was extracted and characterized several proteins that have tensioactive properties and complement the lipid tensioactive properties, and these include PS-A, PS-B, PS-C, PS-D, and the like.

When there are not sufficient physiological quantities of PS and/or when the PS film is altered, it presents respiratory problems that produce clinical charts with severe characteristics such as generically denoted respiratory distress syndrome (RDS) and adult respiratory distress syndrome (ARDS).

The patients that exhibit the above mentioned syndrome are treated by providing exogenous PS, a product that is obtained by washing the pulmonary tract of healthy animals (especially pork and in less abundance cows or sheep) with saline solutions and further fractionation, purification and lyophilization. Given that the exogenous PS is an expensive product, the treatment with natural exogenous PS, in general, is limited to the treatment of premature infants.

The high price of the natural exogenous PS has motivated the search for synthetic exogenous surfactants that are less expensive. There are several products with the tensioactive characteristics of natural PS, such as mixtures of dypalmitoilphodphatidylcoline (DPPC), hexadecanol and phyloxapol (Exosurf), phosphatidylglycocerol (ALEC), etc.

Exogenous PS is a product that results from the extraction, by aqueous saline solution from a pig's respiratory system or from a cow or sheep. Also from lung divided in sheets with later fractionation and purification, and in accordance with a sequence of operations of filtration, dialysis, ion exchange chromatography and exclusion chromatography in order to arrive at a lyophilized product or product in dilute solutions with a cost in the order of 4,000 to 5,000 dollars per gram.

SUMMARY OF THE INVENTION

We have developed a natural pulmonary surfactant by a new much simpler method that produces a product analogous to the one obtained by the conventional method of extraction and purification, which is much less costly, of the order of ⅛ to ⅒ of natural PS extracted by prior art methods.

The object of this invention is the production of a product that contains liposoluble lipids and proteins, in a chloroform solution, useful for preparing exogenous PS. These liposoluble lipids and proteins obtained from washing the bronchial-alveoli of pork, cows or sheep with slightly hypertonic saline solutions by a method that includes:

I. Fractionating by means of differential centrifugation the liquid obtained by the washing operation. This centrifugation is done in at least two scaled operations, the first made at a low velocity, in the range of 500–10,000 g from which is obtained the liquid phase and the pellets are discarded. In the next stage the centrifugation is done at high velocity in the range of 8,000–10,000 g, salvaging the formatted pellet.

II. Fractionating by centrifugation at 8,000–10,000 g the suspension formed when the pellet of the previous stage is suspended in a saline solution buffered at pH: 7.2–7.4, saving the residue and repeating this operation until the pellets are white in color and have a creamy consistency.

III. Suspending the pellet in a water soluble polar solvent such as acetone, saving the residue after centrifugation at 8,000–10,000 g. This pellet is made up of crude exogenous pulmonary surfactant.

IV. Dissolving the crude exogenous pulmonary surfactant pellet from the previous stage in a medium insoluble in water such as chloroform or dichloromethane:methanol in a 2:1 ratio and extracting the solution formed with slightly hypertonic saline solution, recuperating the yellow liquid phase by filtration, from which the solvent is eliminated and the solid pellet is dissolved in chloroform to form the product of the present invention, finally it is filtered by a porous membrane of 0.80, 0.45 and 0.22 $\mu$m.

Another objective of this invention is a method for obtaining a product that contains the liposoluble lipids and proteins extracted from the liquid obtained from washing the bronchio-alveoli of pork, cows or sheep with slightly hypertonic saline solutions obtained with the procedure indicated: lyophilized and dosaged in units or kits for instant reconstitution that involves:

I. Fractionation by means of differential centrifugation of the liquid obtained by the washing operation. This centrifugation is done in at least two scale operations, the first made at low velocity, in the range of 500–1,000 g, from which is obtained the liquid phase and the pellets are discarded: the next stage the centrifugation is done at high velocity in the range of 8,000–10,000 g, salvaging the formatted pellets.

II. Fractionation by centrifugation at 8,000–10,000 g produces the suspension formed when the pellet of the previous stage is suspended in a saline solution buffered at pH: 7.2–7.4, the pellet is recovered and repeating this operation until the pellets are white in color and have a creamy consistency.

III. Suspending the pellet in a water soluble polar solvent such as acetone, saving the pellet after centrifugation at 8,000–10,000 g. This pellet is the crude exogenous surfactant pulmonary.

IV. Dissolving the crude exogenous pulmonary surfactant pellet from the previous stage in a medium insoluble in water such as chloroform or dichloromethane:methanol in a 2:1 ratio and extracting the solution formed with slightly hypertonic saline solution, recuperating the yellow liquid phase by filtration, from which is eliminated the solvent and solid residue, dissolving in chloroform to form the product of the present invention, finally it is filtered by porous membrane of 0.80, 0.45 and 0.22 µm dimension.

Another object of this invention it is to obtain a product administrable by inhalation, useful for the treatment of cases with deficient pulmonary ventilation characteristic of the RDS and ARDS syndromes that involves the product obtained from the lyoliphiliation of the exogenous PS in a pharmaceutical acceptable vehicle. Such as physiological solutions having effective therapeutic concentrations and the possible combination with other therapeutic agents such as antibiotics, bronchidilators, antimicoticos, etc.

Another object of the present invention is a product useful in obtaining images from pulmonary centellography that include: Resuspension in an acceptable vehicle such as a physiological solution, the material obtained from the lyophilization of the product mentioned above in combination with radionuclei.

In addition another object of this invention is a product useful in obtaining images from pulmonary centellography in which the radioisotope is 99 mTc in combination with a reductor such as Sn2+(stannic chloride).

DETAILED DESCRIPTION OF THE INVENTION

The following schemes I and II illustrate in detail the required operations corresponding to the present invention for processing the liquid from the washed bronchioalveoli of animals whose pulmonary surfactant is biocompatible with man.

SCHEME I: Obtaining the Crude Pulmonary Surfactant
I. Liquid obtained from washed bronchus-alveoli.
II. Sequential filtration with 100, 50 and 5 micron membranes (4.5 liters).
III. Centrifugation at 500 g for 5 minutes.
   Discard solid pellet.
   Opalescent liquid phase.
IV. Centrifugation at 8,500 g for 1 hour.
   Discard liquid phase.
   Semi-solid pellet.
   Buffer solution.
V. Centrifugation at 8,500 g for 1 hour.
   Discard liquid phase.
   Semi-solid pellet.
   Buffer solution.
VI. Centrifugation at 8,500 g for 1 hour.
   Discard liquid phase.
   White semi-solid pellet.
VII. Suspension in a polar solvent water soluble (acetone).
VIII. Centrifugation at 8,500 g for 15 minutes.
   Discard liquid phase.

Crude Pulmonary Surfactant

Solution buffer: NaCl 150 mM–CaCl2 2 mM; Tris 50 mM (pH: 7.43).
Scheme II: Obtaining the Pulmonary Surfactant in Chloroform Solution Crude Pulmonary Surfactant Ia. chloroform-methanol 2:1
   Agitation
   Solution slightly Hypertonic. NaCl
   Discard supernatant phase IIa. Filtration
   Discard filtration residue
   Pulmonary surfactant in chloroform phase (yellowish)
IIIa. Evaporation of residuals solvent (chloroform)
   Evaporation until dry (reduced pressure)
   Solid residue (Pulmonary surfactant)
IVa. Redissolution in chloroform
Va. Sequential Filtration of the chloroform solution throughout membranes of 0.80; 0.45 and 0.22 microns.
VIa. PULMONARY SURFACTANT
   Sterile chloroform solution
VIIa. Fractionation, lyophilization, etc.

The liquid from washing, that is processed in the present invention, is an aqueous liquid that contains soluble components and dispersible components extracted from pigs, cows or sheep and whose composition has been mentioned above. Healthy animals are chosen, preferably young ones, from which the entire respiratory apparatus is used, excluding the top areas.

The washing is done in several successive stages (3 or 4 are sufficient) with slightly hypertonic saline solutions, with a volume that depends on the size of the animal.

The slightly hypertonic saline solution used for the bronchio-alveoli washing, are principally sodium chloride solutions of 0.9–1.2% p/v, preferably 1.0% p/v.

In the first stage, the liquid obtained after washing is filtrated (stage II of scheme 1) in order to eliminate small clots, tissues parts, cellular fragments, etc. This filtration operation is done in scaled form, with membranes of decreasing porous size, from 100 microns in the first filtration to 5 microns in the final filtration from where an opalescent liquid is obtained.

One of the novelties of this invention resides in the stages of differential centrifugation—stages III and VIII from scheme I—of the filtered washing liquid that results in the purification crude pulmonary surfactant. In this invention, differential centrifugation implies that the centrifugation of the washing liquid is conducted in at least two successive stages, differentiated for the application of increasing centrifugation speed with discard of the residues and recuperation of the supernatant phase in the first operation of centrifugation and with discard of the supernatant phase and recuperation of the residues of the second operation of centrifugation, processes in the following operations (steps IV to VI). The method of the invention consists of two centrifugation operations, the first done at no more than 1,000 g preferably between 500 and 1,000 g, most preferably at 500 g and the following centrifugation at no less than 8,000 g, preferably at 8,000–10,000 g, most preferably 8,500 g. The pellet resulting from the final centrifugation is a soft mass, which it is re-suspended in a buffer solution (NaCl 150 mM, CaCl2 2 mM, tris 50 mM; pH: 7.4) (steps V, VI) and again it is centrifuged producing a semisolid mass. Re-suspending the semisolid mass, recuperated with the above mentioned buffer solution and centrifuging until a homogenous mass of creamy white color is obtained.

In the following stage this soft, white, creamy mass is re-suspended with a water soluble polar solvent, such as acetone (stage VII). The amount of solvent used is 4–6 ml, preferably 5 ml, of acetone per gram of the white yellowish mass. The solution is then centrifuged at 8,500–10,000 g, preferably 8,500 g.

From this final centrifugation step, the crude pulmonary surfactant (SP-crude) is obtained in step VIII, the supernatant liquid phase is discarded. The SP-crude can be processed immediately following the sequence of Scheme II, or stored at low temperature (at 0° C., or preferably between 0° C. and −5° C.).

The exogenous SP is recovered from Step VII through a series of steps starting with the dispersion of the PS-crude through an insoluble solvent in water (step Ia of scheme II) below the boiling point, which is pharmaceutically acceptable. For example, chloroform or dychloromethane, or preferably chloroform or chloroform-methanol 2:1 in volume.

The solution that is formed is extracted with aqueous NaCl (step Ia) in a solution that is physiological or slightly hypertonic (1% p/v) under constant agitation.

From decanting three phases are separated: a supernatant liquid phase (discarded by decanting or suction), an insoluble mass located at the phase boundary (discarded by filtration) and a lower phase, yellow in color which contains the lipids and liposoluble proteins (step IIIA).

This yellow solution (solution of chloroform with reduced methanol content) is concentrated by evaporation at reduced pressure (lyophilization or in a rotovapor) at 37° C.±2° C. results in a solid residue of PS purified extensively with methanol, which is dissolved in chloroform, in order to form a chloroform solution (stage IVa) which is finally filtered to separate out the particles having diameters above 0.22–0.25 $\mu$m (particles, bacteria, etc.). Preferably the last filtration step is made in a sequential manner using membranes having 0.80, 0.45 and 0.22 $\mu$m pore size.

The product of the last stage constitutes the chloroform solution of the present invention step Va that contains the liposoluble lipids and proteins of the pulmonary surfactant extracted from the washing liquid. This is a clear sterile solution, that can be stored and transported at temperatures below 0° C. From this chloroform solution it is possible to obtain the mentioned liposoluble lipids and proteins such as the exogenous pulmonary surfactant in lyophilized dosage or as a lyophilized product in bulk.

Such doses are obtained, for example, by fractionation of a chloroform solution of this invention in sterile containers, eliminating the solvent for lyophilization. Units or kits may be obtained that contain exogenous PS, lyophilizaded in doses reconstitutible for administrated by inhalation, endotracheal or nebulization.

The following example, given as an illustration, shows how the invention can be used.

EXAMPLE 1

1. Extraction from the lungs:

Young and healthy animals (pigs, cows or sheep) are selected from the refrigerator, their lungs are carefully extracted to avoid damage to the air pathways and the lungs. Once they have been obtained, the lungs are placed in coolers (2° to 8° C.) for their shipping and storage until their washing. The time period between extraction of the lungs and when they are washed cannot exceed 48 hours.

2. Bronchial-Alveolar Washing of the Lungs:

The lungs which are going to be washed are carefully examined, and any lung which is not in perfect condition is discarded. Then, the trachea is connected to a container which has 4 liters of Solution A, and the following procedure is done for each lung:

a) The left lung is filled with 1 liter of Solution A, it is softly stroked for 5 minutes and then the washing liquid is extracted by vacuum (at least 80% of the original volume).

b) The same is done with the right lobe.

c) Steps a) and b) are repeated until the 4 liters of washing liquid is exhausted.

The washing liquid is sequentially filtered through filtration bags with a pore size of 100, 50, 10 and 5 microns, and it is then centrifuged.

3. Extraction of the Raw Surfactant:

a) The first centrifugation is done for 5 minutes, at 500 g, obtaining:

Superior phase: liquid and opalescent (suspension 1), which is preserved

Inferior phase: semi-solid, which is discarded.

b) Suspension I is centrifuged for 1 hour at 8,500 g, obtaining:

Superior phase: liquid, which is discarded.

Inferior phase: semi-solid (pellet I), which is retained.

c) Pellet I is re-suspended in Solution B, keeping a ratio of 10 ml per gram of pellet I. Then, it is centrifuged for 1 hour at 8,500 g, obtaining:

Superior phase: liquid, it is discarded.

Inferior phase: semi-solid (pellet II), it is retained.

d) Step c) is repeated as many times as necessary until a semi-solid white creamy inferior phase is obtained (pellet III).

e) Pellet III is re-suspended in Solvent A, keeping a ratio of 5 ml per gram of pellet III, and then it is centrifuged for 15 minutes at 8,500 g, obtaining:

Superior phase: liquid, it is discarded.

Inferior phase: solid (pellet IV), it is retained.

4. Obtention of the Surfactant in Solution:

The pellet IV is dissolved in X ml of Solution C (X=4 times the weight in grams of the pellet I). It is strongly agitated for a period of 5 minutes. Y ml of Solution A (Y=weight in grams of pellet I) is then added and is strongly agitated for another 5 minutes and is then allowed to rest, 3 phases are obtained:

Superior phase: aqueous

Intermediate phase: semi-solid

Inferior phase: surfactant in solution, yellow color.

The superior phase is eliminated by suction. Then the intermediate and inferior phases are separated and by filtration and the residues are eliminated; what remains is the surfactant in solution. Subsequently the solvent B is eliminated by evaporation at reduced pressure in a rotavapor with a thermostatic bath a (37±2)° C. A solid residue is obtained that is dissolved in 2 ml of solvent B (Z=weight of residue in mg/20). The resultant surfactant in solution is sequentially filtrated with membranes having 0.80, 0.45 and 0.22 $\mu$m pore size in a laminar flux and deposited in a sterile container and stored at temperatures below 0° C.

Solution A: Sodium Chloride a 1% in distilled water.

Solution B: Sodium Chloride 150 mM, Calcium Chloride 2 mM, Tris 50 mM (pH:7.4).

Solution C: Chloroform:Methanol (2:1).

Solvent A: Acetone.

Solvent B: Chloroform.

The exogenous PS (EPS), especially the one originated from pig's lungs, may be used in the treatment of the respiratory insufficiency, of premature neonates RDS with excellent results.

Less often the EPS is utilized in the treatment of certain pulmonary phatologies in adults (pulmonary infections, insufficient respiratory, ARDS, etc.) such treatment has been limited, as was mentioned, because the high price of a dose.

The EPS may be utilized in the clinical investigation of pulmonary ventilation. This also can be obtained with difficulty, through the centellography by inhalation of aerosols that transport radioactive elements: 111Xe, 85Kr, 113ln, etc. In this case the patient inhales radioactive aerosols (radio aerosols) by means of nebulization for a time long enough to obtain a deposit no bigger than 3 mCi. It is possible to produce centellografic images that allow for the identification of functional and dynamic aspects of the pulmonary respiration of the patient (arterial obstruction, arterial hypertension, etc.).

EPS of the present invention can be utilized as a vector to detect radioactive elements for the study of pulmonaryphisiophatology. In this aspect, the EPS of this invention can be utilized in combination with radionuclei in formulations administrated by inhalation to do research on the pulmonary physiology.

In spite of the fact that the EPS of the present invention is an adequate transport vehicle for any of the conventional radionuclei, the product shows excellent results when 99 mTe stabilized with an appropriate agent reductor, such as Sn 2+, is used as is illustrated in the following example:

EXAMPLE 2

2.0 mg of EPS, lyophilized, of the present invention, labeled with 99 mTc and stabilized with Sn 2+(SnCl2) in physiological solution was given to each of a group of 10 subjects. In such a group, 4 of the subjects were smokers; the ventilation was made with an Ultra Vent Kit apparatus, during 2 to 3 minutes with an activity of 110 Mbq. Later the respective pulmonary centellographs was obtained. The experiment was repeated with the same subject, a posterior examination, (72 hours later) but using a conventional radiopharmaceeutical (DTPA with 99 mTc), with a ventilation time of 4 to 5 minutes and an activity of 555 Mbq.

The analysis of the centellographic imagines that show the state of pulmonary ventilation demonstrated that use of the EPS of the present invention is superior in 7 out of the 10 subjects studied.

These results demonstrate that the combination 99 mTc with the EPS of the present invention is excellent for the study the pulmonary physiology and physiophatology with smaller and less expensive radioactive doses.

Stability assays have shown that the lyophilized EPS product maintains its properties without change during 3 months, storage in normal condition in standard proportion of 2 mg of EPS and 100 $\mu$m of $Sn^{2+}$.

What is claimed is:

1. A method for purifying exogenous pulmonary surfactant comprising the steps of:

washing bronchio alveoli with 0.8–1.2% p/v saline solution thereby forming a first solution;

fractionating the first solution originated in the washing step by differential centrifugation, whereby a first pellet is produced;

resuspending the first pellet in a buffer and further fractionating it by first centrifugation whereby a second pellet is produced;

resuspending the second pellet in a polar solvent and fractionating the resultant second solution by a second centrifugation whereby a third pellet is produced;

dissolving said third pellet in a water-insoluble second solvent forming a third solution;

extracting said third solution with a hypertonic saline solution; and collecting the bottom liquid phase resulting from said extraction.

2. The method of claim 1 wherein said differential centrifugation is at least two centrifugations: low speed centrifigation after which the supernatant is recuperated, and subsequent high speed centrifugation after which a first pellet is recuperated.

3. The method of claim 2 wherein the low speed centrifugation is at 500 g.

4. The method of claim 2 wherein the high speed centrifugation is at 8500 g.

5. The method of claim 1, wherein the saline solution is a 1% p/v aqueous solution of sodium chloride.

6. The method of claim 1, wherein the first solution is filtered successively using membranes of 100, 50, 10 and 5 $\mu$m diameter pore size.

7. The method of claim 1, wherein the saline solution is buffered with a solution of sodium chloride 150 mM, 2 mM calcium chloride and Tris 50 mM; pH 7.4.

8. The method of claim 1, wherein the polar solvent is acetone.

9. The method of claim 1, wherein the resuspension of the second pellet is made with chloroform:methanol 2:1.

* * * * *